United States Patent
Kittelson et al.

(10) Patent No.: US 7,628,007 B2
(45) Date of Patent: Dec. 8, 2009

(54) ONBOARD DIAGNOSTICS FOR ANOMALOUS CYLINDER BEHAVIOR

(75) Inventors: David B. Kittelson, Minneapolis, MN (US); Brian C. Krafthefer, Stillwater, MN (US); Hongbin Ma, Columbus, IN (US); Michael L. Rhodes, Richfield, MN (US)

(73) Assignee: Honeywell International Inc., Morristown, NJ (US)

( * ) Notice: Subject to any disclaimer, the term of this patent is extended or adjusted under 35 U.S.C. 154(b) by 410 days.

(21) Appl. No.: 11/612,183

(22) Filed: Dec. 18, 2006

(65) Prior Publication Data
US 2007/0137177 A1   Jun. 21, 2007

Related U.S. Application Data

(60) Provisional application No. 60/753,091, filed on Dec. 21, 2005.

(51) Int. Cl.
*F01N 3/00* (2006.01)
(52) U.S. Cl. .............................. 60/277; 60/274; 60/276; 60/295; 60/297; 73/118.1
(58) Field of Classification Search ................... 60/274, 60/276, 277, 285, 295, 297, 301; 73/118.1
See application file for complete search history.

(56) References Cited

U.S. PATENT DOCUMENTS

| 6,363,771 | B1 | 4/2002 | Liang et al. |
|---|---|---|---|
| 6,971,258 | B2 * | 12/2005 | Rhodes et al. ............. 73/28.01 |
| 7,155,334 | B1 * | 12/2006 | Stewart et al. ............. 701/114 |
| 7,334,401 | B2 * | 2/2008 | Cheng ........................ 60/297 |
| 7,389,773 | B2 * | 6/2008 | Stewart et al. ............. 123/672 |
| 2002/0116917 | A1 | 8/2002 | Glugla |
| 2003/0131587 | A1 | 7/2003 | Kawamura |
| 2004/0039514 | A1 | 2/2004 | Steichen |
| 2004/0162666 | A1 | 8/2004 | Bidner |
| 2005/0125139 | A1 | 6/2005 | Keller et al. |
| 2005/0188681 | A1 | 9/2005 | Emi et al. |
| 2005/0241298 | A1 | 11/2005 | Bayerle |
| 2006/0016246 | A1 | 1/2006 | Rhodes et al. |

OTHER PUBLICATIONS

International Preliminary Report for PCT/US2006/048284, dated Jun. 24, 2008 (9 pages).

David B. Kittelson, et al., "Origin of The Response of Electrostatic Particle Probes" (SAE Technical Paper Series, No. 870476), Society of Automotive Engineers, Feb. 1987.

PCT International Search Report and Written Opinion for corresponding international application No. PCT/US 06/48284, Oct. 31, 2007.

* cited by examiner

*Primary Examiner*—Binh Q. Tran
(74) *Attorney, Agent, or Firm*—Kris T. Fredrick

(57) ABSTRACT

Method and system of onboard diagnostics in engine emissions monitoring, particularly for detecting anomalous cylinder behavior. In some embodiments, at least one sensor in the exhaust path measures electric charge that is indicative of particulate matter. In some embodiments, at least one sensor measures oxides of nitrogen. The indications of instantaneous emissions can be used to effect real-time adjustments in engine control, and can be logged for maintenance purposes.

22 Claims, 10 Drawing Sheets

ONBOARD DIAGNOSTICS FOR ANOMALOUS CYLINDER BEHAVIOR

This invention claims the benefit of the filing date of U.S. Provisional Application Ser. No. 60/753,091 filed on 21 Dec. 2005, incorporated herein by reference.

This invention is related in part to work performed with government support under DE-FC04-02AL67636.

BACKGROUND

Emissions regulations worldwide emphasize reducing fine particulate matter emissions. It appears that fine particles are more strongly linked with adverse health effects than are large particles, and engines are predominant sources of fine particles. Indeed, changes in engine technology to reduce particle mass emissions has led to dramatic increases in the number of tiny particles (too small to constitute much mass) emitted. The nuclei mode particles range in diameter from 5-50 nanometers. They consist of a mix of sulfuric acid and partially burned fuel and lubricating oil. Most nuclei mode particles are not formed until the exhaust combustion products dilute and cool in the atmosphere, when the vapor phase precursors of nuclei mode particles are more likely to undergo gas to particle conversion.

In order to meet future emissions standards, future diesel engines probably will have to be fitted with sophisticated combustion control systems and, probably, aftertreatment systems including particle filters and traps. An effective exhaust particulate sensor can provide information to abet the reduction of particulate emissions from the engine and, consequently, to make traps and other aftertreatment devices more feasible. The particulate traps could be smaller or could regenerate less often, reducing the expense and the penalty on fuel economy.

It is also desirable to minimize oxides of nitrogen in engine emissions. However, it is well known that reducing particulate matter in engine exhaust can result in greater oxides of nitrogen and vice versa. Therefore, tradeoffs are necessary, and more information about the makeup of engine exhaust will assist in achieving optimal results.

Existing engine emission sensors monitor long term trends in overall engine emissions (1-10 seconds in duration) or integrate total emissions over a fixed test cycle. However, in many engines, one or two cylinders contribute a majority of the emissions with these peaks exceeding emissions standards. Testing by the applicants showed considerable real variation in engine emissions from cylinder to cylinder and from cycle to cycle. That effect is masked when averaged across all cylinders.

Therefore, this invention uses sensors to instantaneously monitor the behavior of individual cylinders or engine cycle behavior in order to measure compliance with current and future emissions regulations that are based on "not to exceed" limits rather than average levels. The information obtained from the sensors also can be used for engine control or maintenance. The information obtained from the sensors can be logged for use during normal maintenance periods, and also can be used to change engine parameters to reduce higher emissions from malfunctioning cylinders.

BRIEF DESCRIPTION OF THE DRAWINGS

Components in the figures are not necessarily to scale.

DETAILED DESCRIPTION OF SOME EMBODIMENTS

Figure 1:
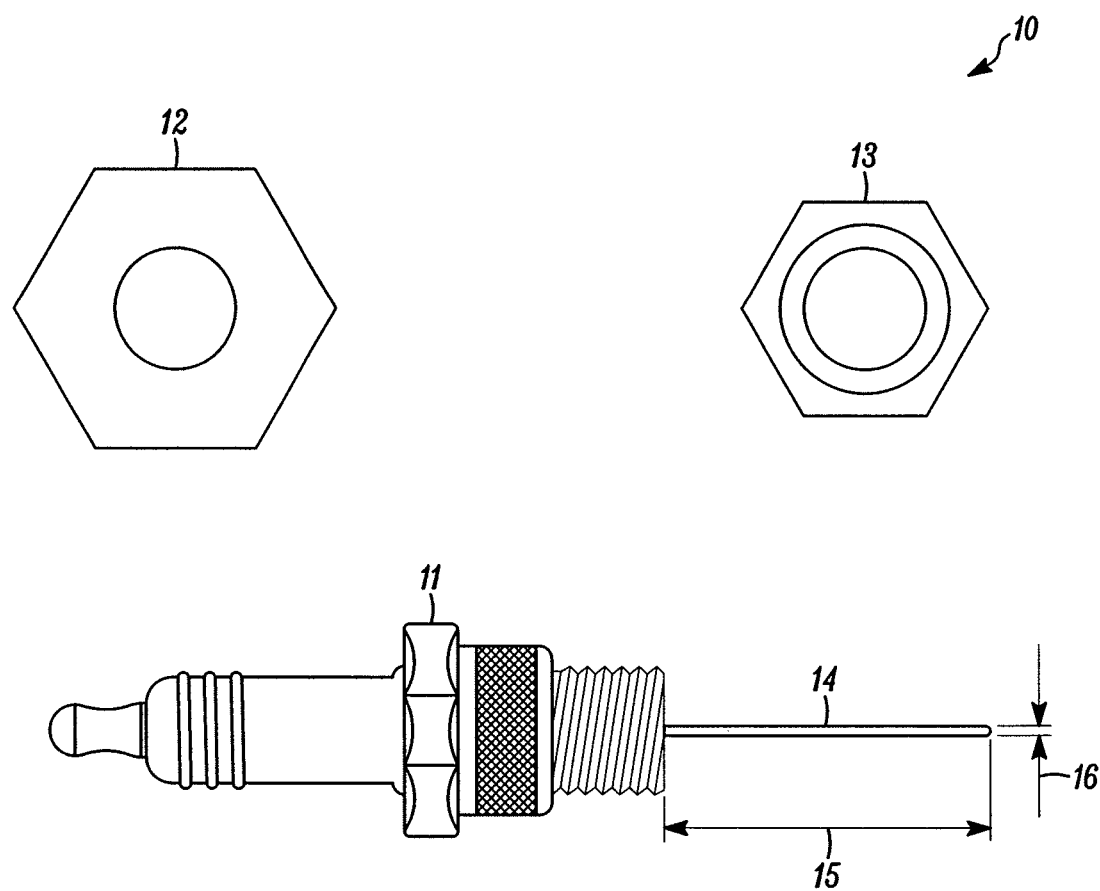
FIG. 1 is an example illustration showing basic components of a particulate matter sensor.

While the present invention is susceptible of embodiment in various forms, there is shown in the drawings and will hereinafter be described some embodiments with the understanding that the present disclosure is to be considered an exemplification of the invention and is not intended to limit the invention to the specific embodiments illustrated or described.

As an example of one embodiment, a sensor can monitor the charge on particulate matter during the exhaust stroke of an engine cylinder. Different electric charge sensors are known in the art. For example, some are contact charge sensors and some are image charge sensors that can measure charge of particles in a passing exhaust stream regardless of contact with the sensor. Some are ion sensors. An example of a sensor for monitoring charge on particulate matter during the exhaust stroke of an engine cylinder is described below. Related technology is described in U.S. Pat. No. 6,971,258, that is incorporated herein by reference. Because charge is a purely electrical phenomenon, the response rate is very high and emissions can be monitored in real-time. Cylinder by cylinder and cycle by cycle monitoring can be achieved.

As an example of one embodiment, the electric charge sensors utilize high-temperature metal rings, disks, or screens, with glass or ceramic electrical feed-through, to provide electrical isolation to the sensed signals. Readout electronic circuits measure the ionization, charge, or current transport, as well as other parameters such as temperature.

As one example, the electric charge sensor can be built upon an automotive spark plug. This approach provides a very good high temperature and high pressure platform that easily can be placed in the engine's exhaust path, such as directly in the engine's exhaust pipe, manifold, or header. If the engine has a turbocharger, the sensor can be placed downstream of the turbocharger. This design is also consistent with low cost, high volume manufacturing. The signal electronics can be provided by a commercial laboratory grade charge amplifier.

Figure 2:
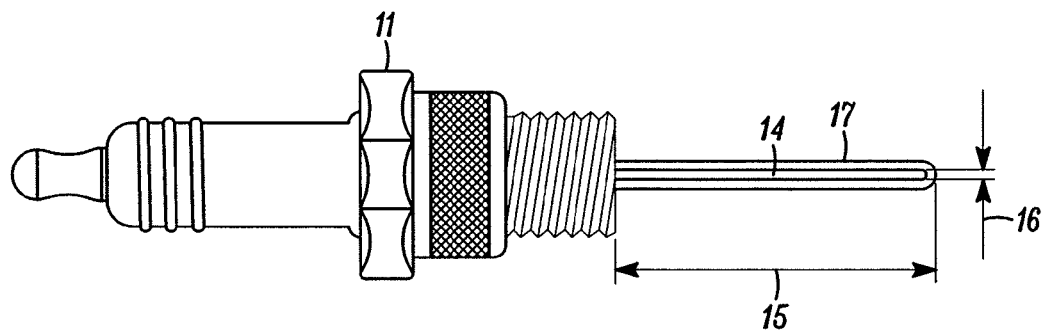
FIG. 2 is a side view of the sensor of FIG. 1.
Figure 3:
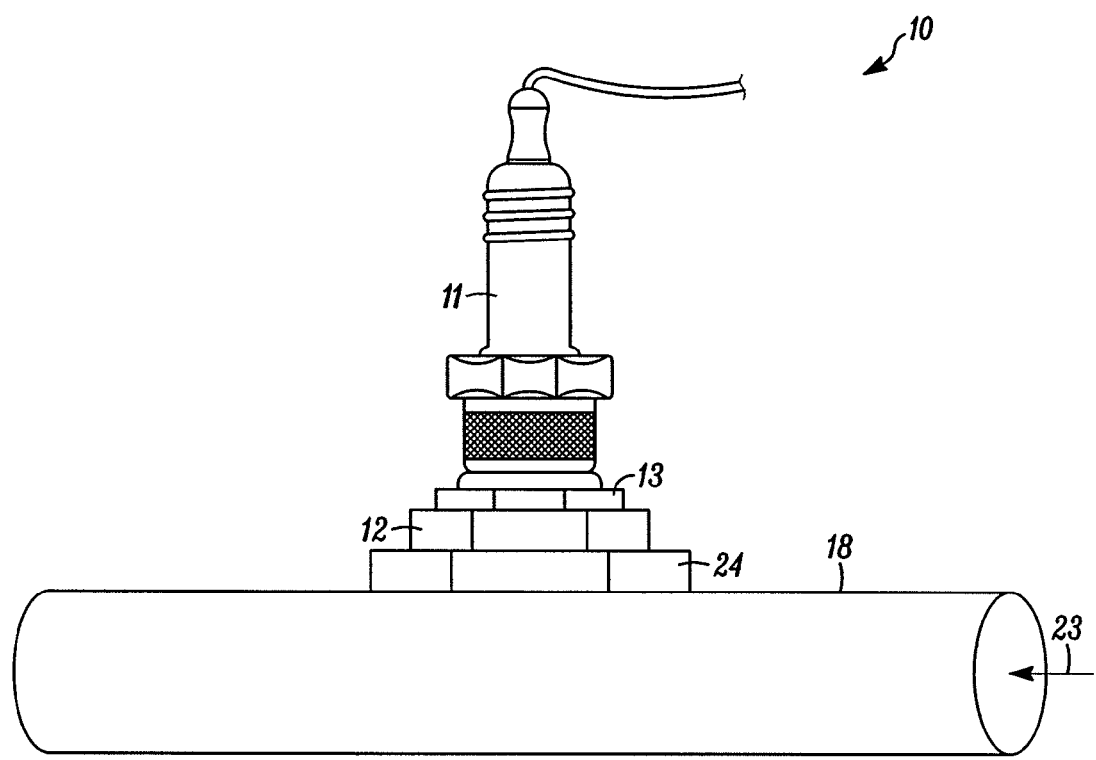
FIG. 3 is an example illustration showing the insertion of the sensor of FIG. 1 in an exhaust pipe.

In the example of FIGS. 1-3, a sensor 10 may use Swageloc® D fittings 12 and/or high temperature ceramic feed-through insulators 13 and/or connectors. A probe 14 of sensor 10 may be placed in the path of the exhaust of the engine. The length 15 and the diameter 16 of probe 14 may be varied depending on the parameters of sensing and the engine.

One development concern was that soot build-up on the sensor probe and operation at very high temperatures would short the signal directly to ground. However, it appears that the active element is passivated with a very thin, nonconductive coating that accounts for the absence of shorting by the soot layer. Therefore, the sensor probe response does not degrade with soot build-up and high temperatures. In the example of FIGS. 1-3, probe 14 is passivated with a very thin non-conductive coating or layer 17 (as illustrated in FIG. 2), that accounts for the lack of electrical shorting by the soot layer accumulated by probe 14 during operation of the engine.

One embodiment of sensor 10 may be a standard spark plug 11 that has the outside electrode removed and has a 4 to 6 inch stainless steel extension 14 of about ⅛ inch diameter welded to the center electrode. Sensor 10 may be mounted in the exhaust stream 23. FIG. 3 illustrates an example of installation of sensor 10 in an exhaust pipe 18. There may be a stainless steel collar 24 welded into the exhaust pipe 18. Collar 24 may be fabricated with an oversized threaded access so that the sensor 10 can be changed easily with other sensors 10 having different probe styles.

In testing, the root mean square value (rms) of the sensor signal was calculated from logged data over many consecutive engine cycles and correlated with the values measured from a Bosch smoke meter, a diffusion charger, a photoelectric aerosol sensor, and a condensation particle counter. There is a very good correlation between the charge sensor's rms value and a Bosch Smoke Number down to about a Bosch number of about 0.1.

Sensors for measuring oxides of nitrogen are known in the art. Such a sensor also can be built on a spark plug and installed in an engine exhaust path.

Figure 4:
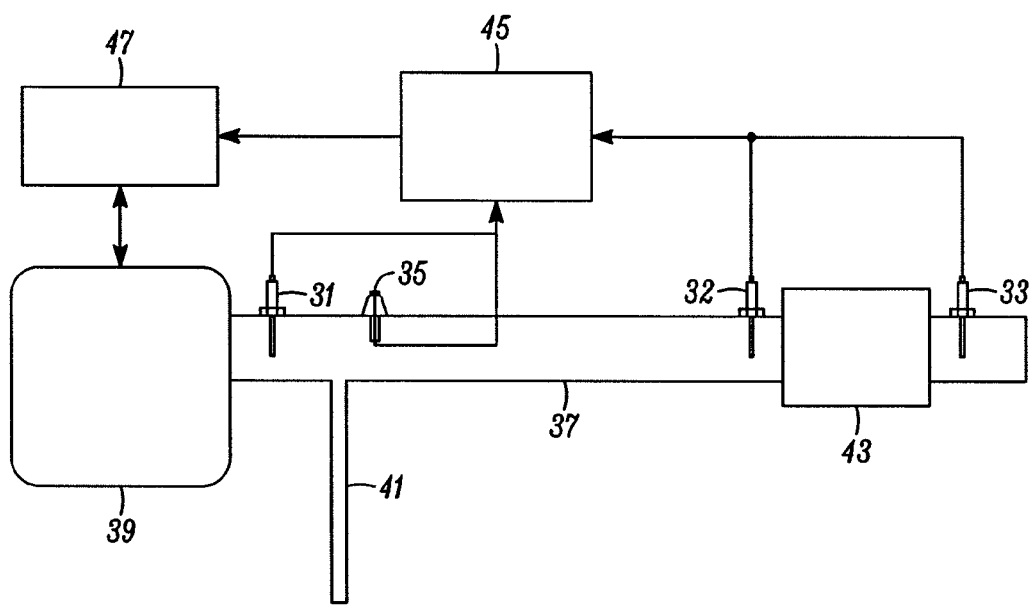
FIG. 4 is an example representation of a system for using onboard diagnostics in engine emissions monitoring, illustrating the location of sensors in an engine exhaust path.

FIG. 4 is an example representation of a system for using onboard diagnostics in engine emissions monitoring, illustrating examples of the location of sensors in an engine exhaust path. Sensors 31, 32 and 33 for measuring particulate matter and sensor 35 for measuring oxides of nitrogen are installed in exhaust pipe 37 from engine 39. Exhaust gas recirculation 41 and a diesel particulate filter 43 are also shown. In addition to generating sensor signals, the system desirably has data processing capability to extract information from the signals on a real-time basis. Therefore, signal processing electronics 45 receive and amplify sensor signals, and provide input to the engine control unit 47. Engine control unit 47 is connected to the engine 39 including its fuel injection and intake manifold system. In addition to the signals from the sensors in the exhaust path, the engine control unit 47 also may receive signals regarding engine parameters such as fuel flow, exhaust gas recirculation, injection timing, needle lift, crankshaft angle, cylinder pressure, valve position and lift, manifold vacuum, fuel/air mixture, properties of the engine air intake, etc. Engine control unit 47 may provide control signals to adjust fuel mixture, injection timing, percent of exhaust gas recirculation, valve control, and so forth. This description is an example (as are the examples described below) of means for obtaining information relating to undesirable emissions in the engine exhaust path (the undesirable emissions including particulate matter, oxides of nitrogen, or both), means for correlating that information with emissions of individual cylinders, and means for reducing emissions of particulate matter or of oxides of nitrogren of a single cylinder—all on a real-time basis.

The rapid sensing of particulate matter and of oxides of nitrogen from cylinder exhaust can be accomplished on the order of milliseconds, and can provide information on cylinder-to-cylinder variations on a real-time basis. This information can reveal a malfunctioning cylinder, and can reveal exhaust dynamics of the engine under different conditions. Diagnostic software can use such information to log cylinder data for use during periodic maintenance, to change individual cylinder input conditions in order to modify individual cylinder exhaust conditions, and to send a warning signal, such as to a user instrument panel, when undesirable emissions from a cylinder exceed a predetermined level. This describes an example of means for tracking engine emissions over time and for providing a real-time indication of an undesirable engine emission concentration in excess of a predetermined level.

Figure 5:
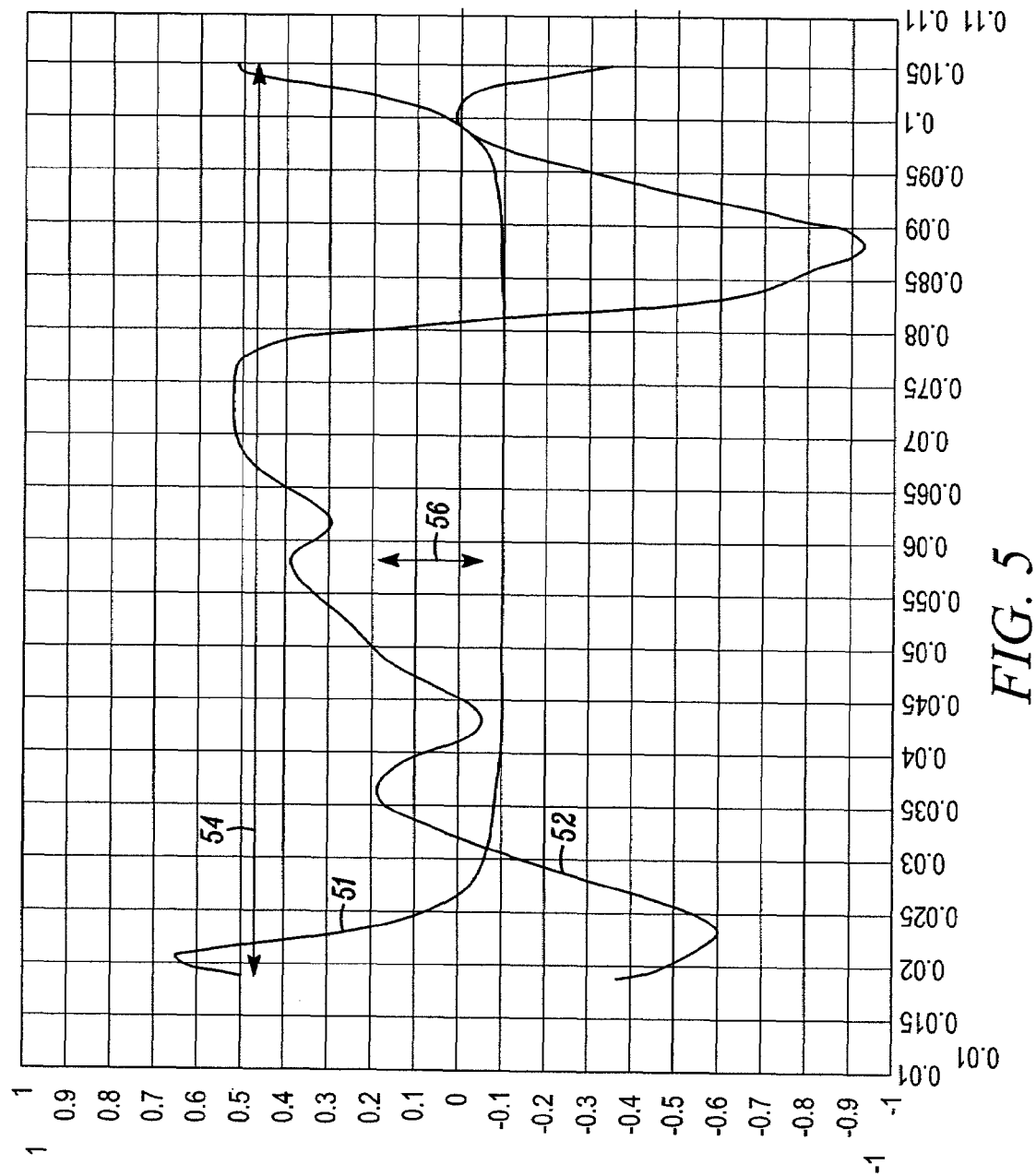
FIG. 5 is a graph displaying experimental data from a test engine.

FIG. 5 is a graph displaying experimental data from a test engine, demonstrating an example of diagnostic information that can be derived from such sensing from engine exhaust. The graph plots voltage versus time in seconds. Signals 51 and 52 were averaged over 11 engine cycles to dampen the effects of spurious noise. Signal 51 was detected from a pressure sensor in one cylinder of the test engine. Line 54 marks off a period of one engine cycle as determined from signal 51. Signal 52 was detected from an electric charge sensor in the exhaust path, located similarly to sensor 31 in FIG. 4. Relative high points in signal 52 occur when minimum particulate matter was detected, and relative low points in signal 52 occur when maximum particulate matter was detected. The relative high point at about 0.036 seconds to the relative low point at about 0.043 seconds shows a peak to peak reading reflecting the particulate matter emitted from one cylinder, as marked off by line 56. The substantially different peak to peak readings apparent in signal 52 demonstrate the wide variation in emissions from the different cylinders. In addition, a noticeable change over time in the peak to peak reading of a particular cylinder is also a valuable diagnostic indicator.

Figure 6:
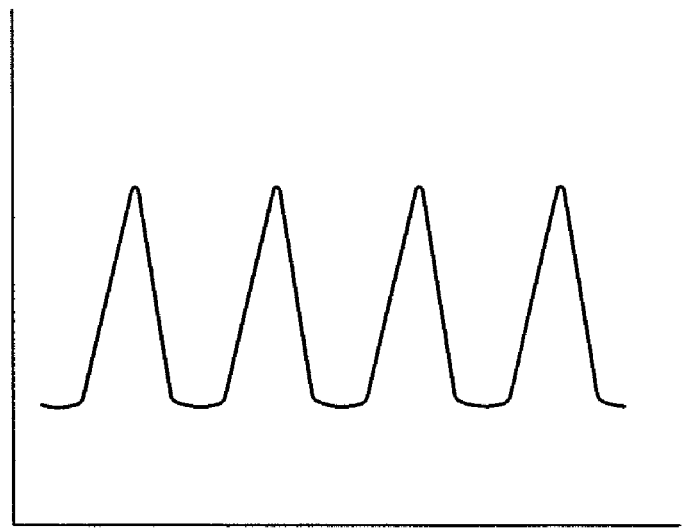
FIG. 6 is a pictorial representation of particulate matter concentration produced during normal engine operation.
Figure 7:
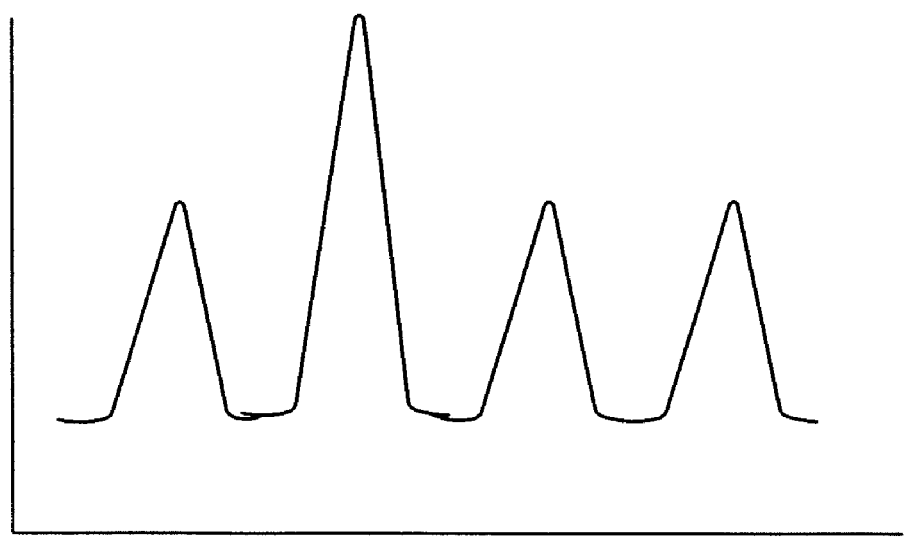
FIG. 7 is a pictorial representation of particulate matter concentration when one cylinder is malfunctioning during engine operation.
Figure 8:
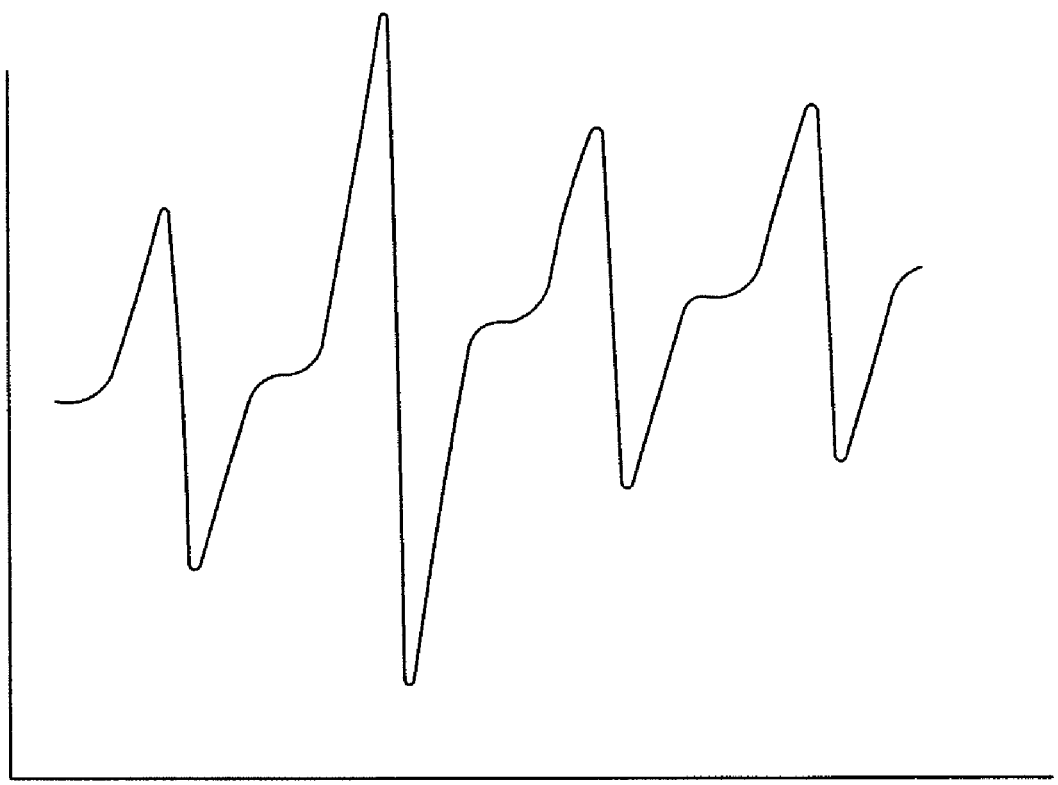
FIG. 8 is a pictorial representation of an electric charge sensor signal during engine operation when one cylinder is malfunctioning.

The principle is illustrated in FIGS. 6 through 8. FIGS. 6 and 7 illustrate examples of particulate matter concentration produced, respectively, during normal engine operation and when one cylinder is malfunctioning during engine operation. When an engine is operating normally, the exhaust particle concentrations from each cylinder will be about the same, as shown in FIG. 6. If one of the cylinders develops a problem, then the particulate matter from this particular cylinder may increase, as shown in FIG. 7. FIG. 8 illustrates an example of a signal such as from an electric charge sensor located similarly to sensor 31 in FIG. 4. FIG. 8 illustrates an example of a signal showing an anomaly in particulate matter during engine operation with a malfunctioning cylinder. From this anomalous signal configuration, data can be logged that will provide useful information to be applied during scheduled maintenance. In addition, operation of the malfunctioning cylinder can be modified while the engine is operating, as a temporary adjustment until maintenance can be scheduled. For example, cylinder operation can be modified by adjusting exhaust gas recirculation 41 or other parameters controlled by engine control unit 47 (such as fuel mixture or injection timing). Therefore, information extracted from the sensors in the exhaust path can be correlated with particulate matter concentrations from individual cylinders on a real-time basis.

As mentioned above, it is also desirable to reduce oxides of nitrogen in engine exhaust, but reducing the concentration of particulate matter can result in greater oxide of nitrogen and vice versa. Different approaches can be taken to control emissions. The onboard diagnostic information available from sensors in the engine exhaust path will assist in optimizing emissions control.

Figure 9A:
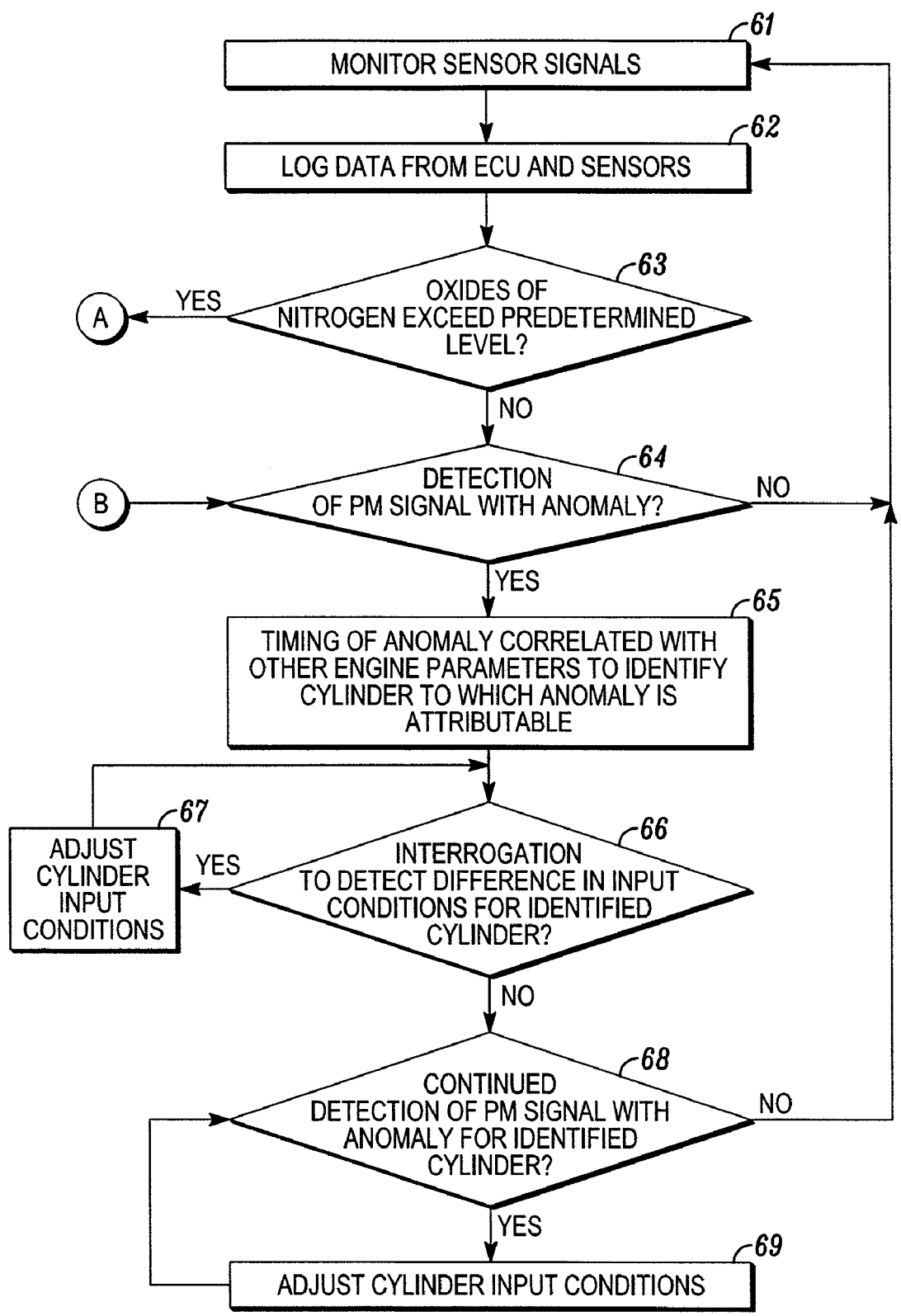
FIGS. 9a and 9b are an example of a diagnostic flow chart.
Figure 9B:
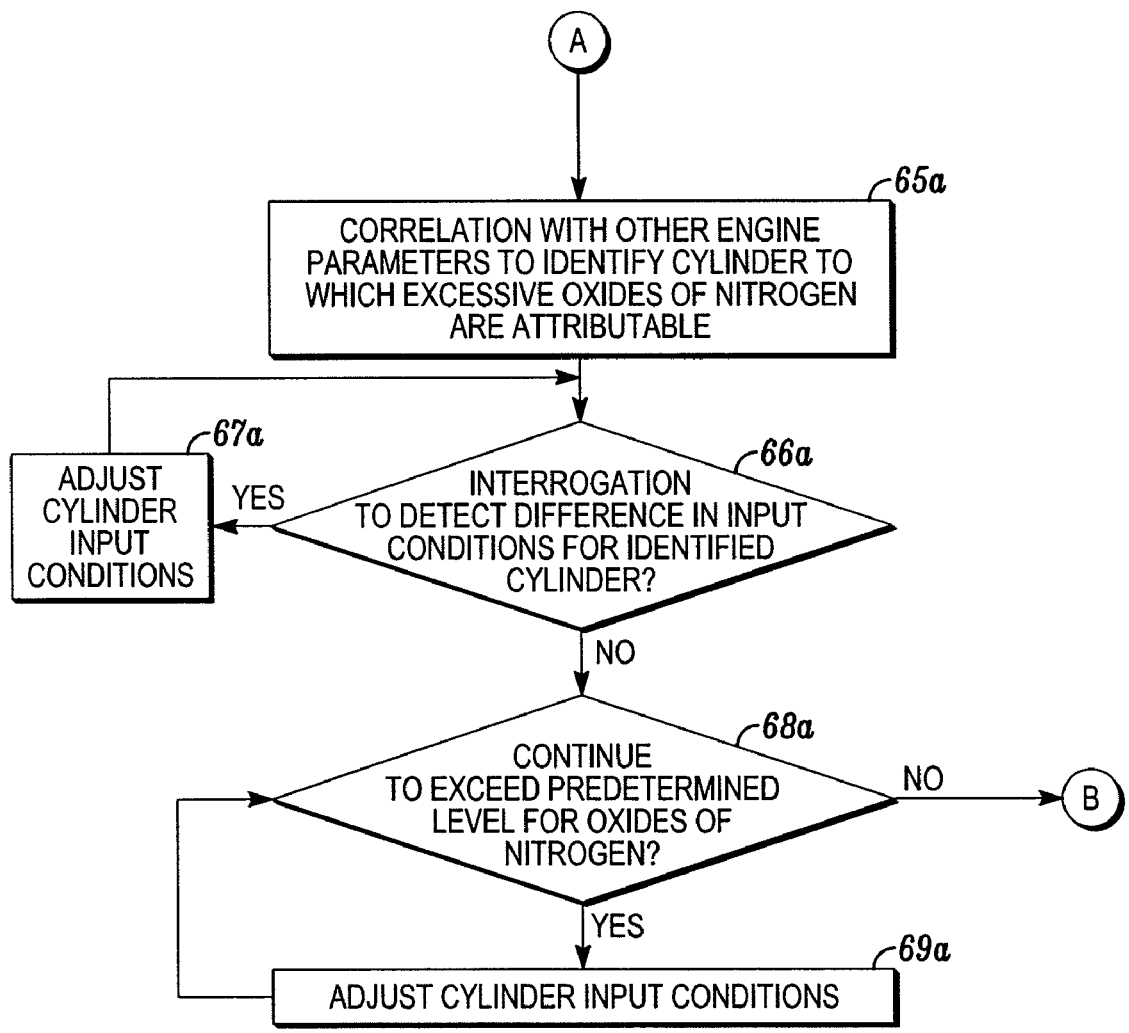

FIGS. 9a and 9b illustrate one example of a diagnostic flow chart. Monitoring (61) of signals from an electric charge sensor 31 and an oxides of nitrogen sensor 35 is maintained by an engine control unit 47. Data from sensors 31 and 35 and from engine control unit 47 are logged (62). The engine control unit 47 detects (63) whether the concentration of oxides of nitrogen exceed a predetermined limit. If they do not, then the engine control unit 47 detects (64) whether there is an anomaly in the particulate matter signal. If there is such an anomaly, then the timing of the anomaly is correlated with other engine parameters to identify (65) the cylinder to which the anomaly is attributable. There is then an interrogation (66) to detect whether there is a difference in input conditions for the identified cylinder. If there is such a difference, then they are adjusted (67) until there is no such difference. There is continued detection (68) of whether the particulate matter signal still shows an anomaly for the identified cylinder. If it does, then cylinder input conditions are adjusted (69) until the anomaly is no longer detected. If the engine control unit 47 detects (63) that the concentration of oxides of nitrogen do exceed a predetermined level, then there is correlation with other engine parameters to identify (65a) the cylinder to which the excessive oxides of nitrogen are attributable. There is then an interrogation (66a) to detect whether there is a difference in input conditions for the identified cylinder. If there is such a difference, then they are adjusted (67a) until there is no such difference. There is continued detection (68a) of whether the oxides of nitrogen continue to exceed the predetermined level. If they do, then cylinder input conditions are adjusted (69a) until the oxides of nitrogen no longer exceed the predetermined level. FIGS. 9a and 9b are merely one example of an applicable diagnostic flow chart.

Typically, the adjustable input conditions may include the fuel mixture or the injection timing to reduce higher emissions from a malfunctioning cylinder. There may be other adjustable input conditions, possibly such as the percent of exhaust gas recirculation or valve control, for example.

Figure 10:
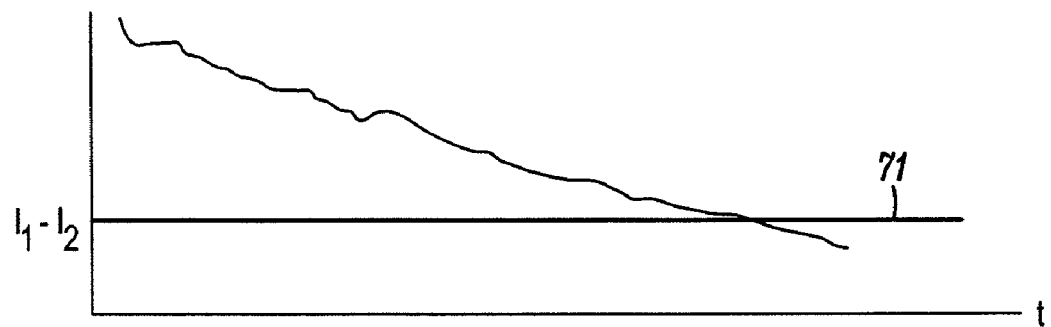
FIG. 10 is a pictorial representation of a difference in signals from two electric charge sensors located, respectively, on both sides of a diesel particulate filter.

As one example of an emissions control strategy, it may be possible to adjust engine timing to reduce oxides of nitrogen, and to use filters to reduce particulate matter. Measuring particulate matter upstream and downstream of a diesel particulate filter is another example of the diagnostic information that can be derived by sensing from engine exhaust. In the example of FIG. 4, there is a diesel particulate filter 43 in the exhaust path. During operation of engine 39, the diesel particulate filter 43 will load and will have to be renewed after a certain amount of time. FIG. 4 illustrates electric charge sensors 32 and 33 located upstream and downstream, respectively, of diesel particulate filter 43. Signals $I_1$ and $I_2$ from sensors 32 and 33, respectively, can be monitored and recorded. The difference in the two signals $I_1$ and $I_2$ will diminish over time as the load of the diesel particulate filer 43 increases. This is illustrated in FIG. 10 which is a pictorial representation of $I_1-I_2$ over time. If that difference becomes less than some predetermined level 71, that may be an indication that it is time to renew the diesel particulate filter 43. An engine control unit 47 also can be programmed to send a warning signal, such as to a user instrument panel, when this occurs. This describes an example of means for detecting when a diesel particulate filter should be renewed.

Figure 11:
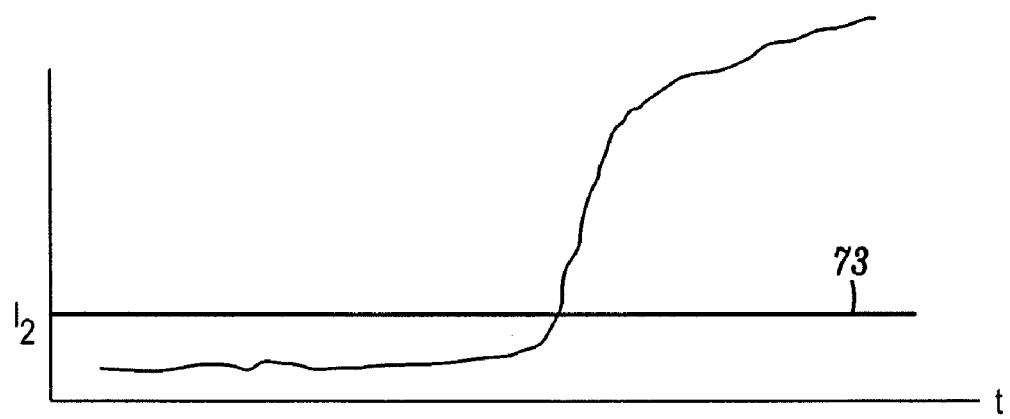
FIG. 11 is a pictorial representation of an electric charge sensor signal downstream of a diesel particulate filter.

FIG. 11 is a pictorial representation of $I_2$ over time. If $I_2$ increases abruptly above some predetermined level 73, this indicates a probable breakthrough of diesel particulate filter 43. This indication of diesel particulate filter failure shows that maintenance is needed to replace the filter. An engine control unit 47 can be programmed to send a warning signal, such as to a user instrument panel, when level 73 is exceeded. This describes an example of means for determining deterioration of effectiveness of a diesel particulate filter in an engine exhaust path.

From the foregoing, it will be observed that numerous modifications and variations can be effectuated without departing from the true spirit and scope of the novel concepts of the present invention. It is to be understood that no limitation with respect to specific embodiments shown or described is intended or should be inferred.

The invention claimed is:

1. An onboard diagnostics system for monitoring engine emissions, the system comprising:
   at least one sensor;
   a data processor;
   each of the at least one sensors being structured and dimensioned for placement in an exhaust path of an engine;
   the data processor being adapted for extraction of information from the at least one sensor on a real-time basis;
   each of the at least one sensors being selected from a group consisting of an electric charge sensor and a sensor for detecting oxides of nitrogen;
   wherein, one of the sensors is an electric charge sensor, and, the information extracted from that sensor can be correlated with particulate matter concentrations from individual cylinders of the engine with the data processor comprising an engine control unit for detecting whether there is an anomaly in the information extracted from that sensor, and for identifying a cylinder to which the anomaly is attributable and which includes:
   receiving at least one signal representative of a cylinder input condition;
   using the cylinder input condition signal to detect whether the input condition of the identified cylinder to which the anomaly is attributable is different than the input condition of other cylinders;
   if the input condition of the identified cylinder is different than the input condition of the other cylinders, adjusting at least one engine parameter until the input condition of the identified cylinder is no longer different than the input condition of the other cylinders; and
   after adjusting the at least one engine parameter until the input condition of the identified cylinder is no longer different than the input condition of the other cylinders, detecting whether the anomaly is still occurring.

2. The onboard diagnostics system as in claim 1, the data processor comprising signal processing electronics for amplifying a signal of the at least one sensor.

3. The onboard diagnostics system as in claim 1, further comprising:
   one of the at least one sensors being a sensor for detecting oxides of nitrogen;
   the data processor being adapted for detecting when a signal of said sensor for detecting oxides of nitrogen exceeds a predetermined level.

4. The onboard diagnostics system as in claim 1, the data processor being adapted for extraction of information representative of an engine parameter selected from a group consisting of fuel flow, percent exhaust gas recirculation, injection timing, needle lift, crankshaft angle, cylinder pressure, valve position, valve lift, manifold vacuum, fuel/air mixture, and an engine air intake property.

5. The onboard diagnostics system as in claim 1, the data processor comprising an engine control unit for sending a control signal to adjust at least one engine parameter on a real-time basis in response to the extracted information.

6. The onboard diagnostics system as in claim 1, the data processor being adapted for sending a control signal to adjust at least one engine parameter selected from a group consisting of fuel mixture, injection timing, percent exhaust gas recirculation, and valve control.

7. The onboard diagnostics system as in claim 1, further comprising a database for logging data indicative of performance by the individual cylinders.

8. The onboard diagnostics system as in claim 1, the data processor being adapted for sending a warning signal when a signal of one of the at least one sensors exceeds a predetermined level.

9. The onboard diagnostics system as in claim 1, further comprising:
   a second one of the at least one sensors being an electric charge sensor;
   the data processor being adapted for sending a warning signal when a difference between respective signals of the first and second ones of the at least one sensors falls below a predetermined level, where the first one of the sensors is located upstream of a diesel particulate filter in the exhaust path and the second one of the sensors is located downstream of the diesel particulate filter.

10. A method for monitoring engine emissions, the method comprising:
    monitoring a signal of an electric charge sensor located in an exhaust path of an engine;
    detecting whether an anomaly occurs in the signal of the charge sensor;
    identifying a cylinder of the engine to which the anomaly is attributable if the anomaly is detected;
    if the anomaly is detected, adjusting at least one engine parameter on a real-time basis until the anomaly is no longer detected and which includes
    receiving at least one signal representative of a cylinder input condition;
    using the cylinder input condition signal to detect whether the input condition of the identified cylinder to which the anomaly is attributable is different than the input condition of other cylinders;
    if the input condition of the identified cylinder is different than the input condition of the other cylinders, adjusting at least one of the at least one engine parameters until the input condition of the identified cylinder is no longer different than the input condition of the other cylinders;
    after adjusting the at least one engine parameter until the input condition of the identified cylinder is no longer different than the input condition of the other cylinders, detecting whether the anomaly is still occurring.

11. The method as in claim 10, the identifying step comprising:
    receiving a signal representative of a selected engine parameter;
    correlating timing of the anomaly with the selected engine parameter.

12. The method as in claim 10, further comprising extracting information from a signal representative of an engine condition selected from a group consisting of fuel flow, percent exhaust gas recirculation, injection timing, needle lift, crankshaft angle, cylinder pressure, valve position, valve lift, manifold vacuum, fuel/air mixture, and an engine air intake property.

13. The method as in claim 10, the at least one engine parameter selected from a group consisting of fuel mixture, injection timing, percent exhaust gas recirculation, and valve control.

14. The method as in claim 10, further comprising logging data indicative of performance by individual cylinders of the engine.

15. The method as in claim 10, further comprising:
    monitoring a signal of a sensor for detecting oxides of nitrogen located in the exhaust path;
    detecting whether a concentration of oxides of nitrogen exceeds a predetermined level.

16. The method as in claim 15, further comprising:
    if the concentration exceeds the predetermined limit, adjusting at least one engine parameter on a real-time basis until the concentration no longer exceeds the predetermined limit.

17. A method for monitoring engine emissions, the method comprising:
    monitoring a signal of a sensor for detecting oxides of nitrogen located in an exhaust path of an engine;
    detecting whether a concentration of oxides of nitrogen exceeds a predetermined level;
    identifying a cylinder of the engine to which excessive oxides of nitrogen are attributable if the concentration of oxides of nitrogen exceeds the predetermined level;
    if the concentration exceeds the predetermined level, adjusting at least one engine parameter on a real-time basis until the concentration is no longer detected as exceeding the predetermined limit and which includes
    receiving at least one signal representative of a cylinder input condition;
    using the cylinder input condition signal to detect whether the input condition of the identified cylinder to which the excessive concentration is attributable is different than the input condition of other cylinders;
    if the input condition of the identified cylinder is different than the input condition of the other cylinders, adjusting at least one of the at least one engine parameters until the input condition of the identified cylinder is no longer different than the input condition of the other cylinders; and
    after adjusting the at least one engine parameter until the input condition of the identified cylinder is no longer different than the input condition of the other cylinders, detecting whether the concentration still exceeds the predetermined level.

18. The method as in claim 17, further comprising extracting information from a signal representative of an engine condition selected from a group consisting of fuel flow, percent exhaust gas recirculation, injection timing, needle lift, crankshaft angle, cylinder pressure, valve position, valve lift, manifold vacuum, fuel/air mixture, and an engine air intake property.

19. The method as in claim 17, the at least one engine parameter selected from a group consisting of fuel mixture, injection timing, percent exhaust gas recirculation, and valve control.

20. The method as in claim 17, further comprising logging data indicative of performance by individual cylinders of the engine.

21. The method as in claim 17, further comprising sending a warning signal when the signal of the sensor exceeds a predetermined level.

22. A method for monitoring engine emissions, the method comprising:
    monitoring a signal of a sensor for detecting oxides of nitrogen located in an exhaust path of an engine;
    detecting whether a concentration of oxides of nitrogen exceeds a predetermined level;
    identifying a cylinder of the engine to which excessive oxides of nitrogen are attributable if the concentration of oxides of nitrogen exceeds the predetermined level;

if the concentration exceeds the predetermined level, adjusting at least one engine parameter on a real-time basis until the concentration is no longer detected as exceeding the predetermined limit and which includes:

monitoring a signal of an electric charge sensor located in the exhaust path;

detecting whether an anomaly occurs in the signal of the charge sensor;

identifying a cylinder of the engine to which the anomaly is attributable if the anomaly is detected;

if the anomaly is detected, adjusting at least one of the at least one engine parameters on a real-time basis until the anomaly is no longer detected and, which further includes:

receiving at least one signal representative of a cylinder input condition;

using the cylinder input condition signal to detect whether the input condition of the identified cylinder to which the anomaly is attributable is different than the input condition of other cylinders;

if the input condition of the identified cylinder to which the anomaly is attributable is different than the input condition of the other cylinders, adjusting at least one of the at least one engine parameters until the input condition of the identified cylinder to which the anomaly is attributable is no longer different than the input condition of the other cylinders; and after adjusting the at least one engine parameter until the input condition of the identified cylinder to which the anomaly is attributable is no longer different than the input condition of the other cylinders, detecting whether the anomaly is still occurring.

* * * * *